United States Patent [19]

Shibanai et al.

[11] Patent Number: 4,732,759

[45] Date of Patent: Mar. 22, 1988

[54] BATH PREPARATIONS AND METHOD FOR PRODUCING THE SAME

[75] Inventors: Ichiro Shibanai, Tokyo; Kenji Nakamura, Osaka, both of Japan

[73] Assignee: Japan Liquid Crystal Co., Ltd., Tokyo, Japan

[21] Appl. No.: 832,746

[22] Filed: Feb. 24, 1986

[30] Foreign Application Priority Data

Jun. 13, 1985 [JP] Japan ............................... 60-129445

[51] Int. Cl.$^4$ ................... A61K 37/54; A61K 35/78; A61K 31/715

[52] U.S. Cl. ........................... 424/94.61; 424/195.1; 514/58; 514/167; 514/251; 514/276; 514/356; 514/458; 514/474; 514/558; 514/725

[58] Field of Search .............. 424/94, 195.1; 514/58, 514/233, 277, 167, 725, 474, 558, 458, 251, 276, 356

[56] References Cited

U.S. PATENT DOCUMENTS

| | | | |
|---|---|---|---|
| 4,292,044 | 9/1981 | Shibania et al. | 44/1 R |
| 4,356,115 | 10/1982 | Shibania et al. | 252/522 A |
| 4,443,323 | 4/1984 | Horikoshi et al. | 288/11 LE |

OTHER PUBLICATIONS

J. Szejtli, Cyclodextrins, pp. 240, 241, 369, 370, 410, 459, 460, 78 and 79, 1981.

*Primary Examiner*—J. R. Brown
*Assistant Examiner*—John W. Rollins, Jr.
*Attorney, Agent, or Firm*—Burgess, Ryan and Wayne

[57] ABSTRACT

A bath preparations comprise a cyclodextrin clathrate compound of vitamin, saccharifying enzyme and other materials of baths. The vitamin may be selected from the group consisting of vitamin A, vitamin B, vitamin C, Vitamin D, vitamin E, vitamin F and vitamin P. The saccharifying enzyme may be mixed with the cyclodextrin clathrate compound of the vitamin or may be insulated from the cyclodextrin clathrate compound of the vitamin.

Method for producing bath preparations comprises contacting vitamin with cyclodextrin to form a cyclodextrin clathrate compound of the vitamin and mixing the cyclodextrin clathrate compound of the vitamin with saccharifying enzyme and other raw materials of baths.

13 Claims, No Drawings

BATH PREPARATIONS AND METHOD FOR PRODUCING THE SAME

TECHNICAL FIELD OF THE INVENTION

The present invention relates to bath preparations, especially bath preparations utilizing cyclodextrin clathrate compond. The present invention also relates to a method for producing the bath preparations.

PRIOR ART

Many kinds of bath preparations have been used to soften hard water so as to facilitate easy cleaning, to add color or fragrance to bath water so as to refresh a person's body and mind, to emollient skins, to soften horniness and dissolve dirt on the skin so as to smooth the skin, or to make effects for refreshing the skin by means of effective principles of hot spring or medicial herbs.

Vitamins are used in cosmetics and, especially, vitamin C has effects for refreshing the skin. Accordingly, if at least one of vitamins is added to bath preparations, it is expected that the effects for refreshing the skin is enhanced while a person has a bath. However, no vitamins have been added to any conventional baths.

OBJECT OF THE INVENTION

An object of the present invention is to provide bath preparations which enhance the effects for refreshing the skin while a person has a bath by adding at least one vitamins to conventional bath preparations.

Generally speaking, vitamins are chemically unstable, and accordingly, if they are directly used in bath preparations, they are destroyed or degrade while the bath preparation are produced or stored. Therefore, another object of the present invention is to provide bath preparations wherein vitamins are not destroyed nor degraded when they are produced or stored, and at least one of the vitamins works effectively when the bath preparations are used.

Still another object of the present invention is to provide a method for producing the bath preparations of the present invention.

SUMMARY OF THE INVENTION

The bath preparations of the present invention are characterized in that they comprise a cyclodextrin vitamin clathrate compound of at least one and other materials of bath preparations.

The method for producing bath preparations of the present invention is characterized by: contacting at least one vitamin with cyclodextrin to form a cyclodextrin vitamin clathrate compound; and mixing the cyclodextrin vitamin clathrate compound with saccharifying enzymes and other raw materials of bath preparations.

Another method for producing bath preparations of the present invention is characterized by: substantially reducing end-groups of maltooligosaccharide syrup; contacting a vitamin with reduced cyclodextrin syrup, which is a mixture of the reduced syrup and cyclodextrin, to form a cyclodextrin vitamin clathrate compound; and mixing the cyclodextrin vitamin clathrate compound with other raw materials of bath preparations.

DETAILED DESCRIPTION OF THE INVENTION

In the bath preparations of the present invention, a cyclodextrin vitamin clathrate compound of at least one vitamin is added to raw materials of baths, which have been conventionally used as baths. Furthermore, a saccharifying enzyme may be mixed with the cyclodextrin vitamin clathrate compound and other raw materials of baths. Alternatively, the saccharifying enzyme may be isolated from the cyclodextrin vitamin clathrate compound while the bath preparations are stored, and the saccharifying enzyme and the cyclodextrin vitamin clathrate compound are poured together in a bath.

The vitamin, which is included in the cyclodextrin to form the cyclodextrin vitamin clathrate compound comprises one or more vitamin selected from the group consisting of vitamin A, vitamins B, vitamin C, Vitamin D, vitamin E, vitamin F and vitamin P.

The cyclodextrin of the present invention may be alpha-cyclodextrin, beta-cyclodextrin, gamma-cyclodextrin, a derivative of cyclodextrin, or a mixture thereof.

Taking into consideration both the molecular weight, i.e., diameter of the molecule, of the vitamins and the cavity of the cyclodextrin, the alpha-cyclodextrin is preferred.

The cyclodextrin may be a powder or a cyclodexrin-containing starch decomposition product. It is preferred to use filtrate obtained through a process described in, for example, Japanese Patent Publication No. 43897/52, wherein Cyclomaltodextrin glucanotransferase created by bacteria belonging to Bacilli is contacted with starch to form cyclodextrin, and the deposited cyclodextrin are separated out, because the filtrate contains a lot of alpha-cyclodextrin. Such a cyclodextrin-containing starch decomposition product is available as, for example, Celdex CH-20, manufactured by Nippon Shokuhin Kako K.K.

The cyclodextrin vitamin clathrate compound, wherein the component of vitamin is entrapped in cyclodextrin, may be produced by way of a saturated aqueous solution method or a kneading method.

More specifically, in the saturated aqueous solution method, a predetermined amount of vitamin or vitamins are added to a saturated aqueous solution of cyclodextrin or a supersaturated aqueous solution of cyclodextrin, and then, the solution is agitated for a time between tens of minutes and some hours, and cyclodextrin vitamin clathrate compound is obtained.

In the kneading method, water or hot water is added to cyclodextrin to form a slurry, and then, a required amount of vitamin or vitamins are added to the slurry. Thereafter, the slurry is agitated well in a kneader for a time between tens of minutes and some hours, and pasty material containing cyclodextrin vitamin clathrate compound is obtained.

The paste produced by the above-described saturated aqueous solution method or kneading method and containing cyclodextrin clathrate compound is rinsed, and then is dried by way of spraying, ventilating or freezing method and powder clathrate compound is obtained. It is noted that the drying operation is carried out at a relatively low temperature so as to avoid destroying the vitamins.

The ratio of the vitamin, which is used as a guest, and the cyclodextrin, which is used as a host, is not limited as long as the vitamin can be included in the cyclodextrin. For example, molar ratio of about 1:1 can be used.

For example, 80 parts by weight of Celdex CH-20 (manufactured by Nippon Shokuhin Kako K.K., malt syrup of cyclodextrin), 20 parts by weight of components of vitamins and water (between 80 and 160 parts by weight) were mixed, and were agitated for several hours at a temperature below 65° C. to form cyclodextrin vitamin clathrate compound. The clathrate compound thus obtained was dried at a relatively low temperature to produce clathrate compound of a powder type.

When a commercially available cyclodextrin containing malt syrup is used to produce a cyclodextrin vitamin clathrate compound, scorching, i.e., oxidation, of the syrup may occur if the treating temperature is high. As a result, there may occur a problem that vitamin cannot be fully included by cyclodextrin. Further, there may occur a problem that a cyclodextrin vitamin clathrate compound cannot be dissociated, i.e., ring opening does not occur, until the temperature reaches a relatively high temperature, when a commercially available cyclodextrin containing malt syrup is used to produce cyclodextrin vitamin clathrate compound.

In such a case, it is preferred that the end-groups of the maltooligosaccharide syrup are almost completely reduced, and that reduced cyclodextrin syrup, which is a mixture of the reduced syrup and cyclodextrin, is used to include vitamin together with cyclodextrin to form cyclodextrin vitamin clathrate compound.

The above-described reduced cyclodextrin syrup, i.e., the reduced syrup containing cyclodextrin, of the present invention is produced in a manner set forth below.

First, reducing end-groups of maltooligosaccharide syrup are almost completely reduced to produce reduced syrup. For example, maltooligosaccharide mixture, such as glucose, maltose or maltoriose, obtained by hydrolyzing starch with acid or enzyme, is hydrogenated under nickel catalyst and high pressure. In this case, it is preferred that the amount (or pressure) of hydrogen is set, for example, between 100 and 200 Kg/cm$^2$, and that the reaction is carried out at a temperature about 70+ and 160° C.

As a result, the reducing end-groups of maltooligosaccharide syrup are hydrogenated and are changed to the sugaralcohol corresponding thereto, and their reducing capability is lost. More specifically, glucose, maltose and maltoriose are changed to sorbitol, maltitol and maltotriitol, respectively, and their reducing capability is lost.

The sugar concentration of malt syrup is usually between 30 and 70%, however, Dextrose Equivalent, D.E., i.e., the ratio of reducible sugar to all the solid content, becomes zero after hydrogenation.

Since the reducing end-groups are lost after hydrogenation, oxidation will not occur readily. Accordingly, the stability against high temperature is increased. Further, the syrup will not be easily colored, since the reaction with amino groups, such as amino acid, i.e., amino carbonyl reaction, does not occur.

The mixture of the above-described reduced malt syrup and cyclodextrin can be used as the reduced cyclodextrin syrup which is used in the method of the present invention.

Preferably, malt syrup containing cyclodextrin, for example Celdex CH-20 or Celdex CH-30, manufactured by Nippon Shokuhin Kako K.K., is hydrogenated in a foregoing manner to produce the reduced cyclodextrin syrup.

In this case, since the cyclodextrin is not reducible and since the Dextrose Equivalent value thereof, (D.E., i.e., the ratio of reducible sugar to all the solid content) is zero, the cyclodextrin is not affected during the hydrogenation process and remains as it is. Contrary to this, the reducing end-groups of maltooligosaccharide syrup, containing glucose, maltose or the like except for cyclodextrin, are hydrogenated and are changed to a sugaralcohol corresponding thereto.

Furthermore, pure alpha-cyclodextrin, beta-cyclodextrin, gamma-cyclodextrin, the derivative of cyclodextrin, or the mixture thereof may be added to the reduced cyclodextrin syrup thus obtained.

Alternatively, after pure malt is reduced, cyclodextrin may be added to the reduced malt syrup to form the reduced cylodextrin syrup.

Then, utilizing the thus obtained reduced cyclodextrin syrup, vitamin or vitamins similar to those described above are included in the cyclodextrin by way of a saturated aqueous solution method or a kneading method similar to those described above, and the cyclodextrin vitamin clathrate compound or the cyclodextrin vitamin clathrate, which has been described above, is produced.

Thereafter, the powder type cyclodextrin vitamin clathrate compound, which was obtained by using the powder type cyclodextrin, the cyclodextrin-containing syrup, i.e., starch decomposition product, or the reduced cyclodextrin syrup, is stirred well with othe raw materials of baths, such as, water softener, materials performing bleaching effect or sterilizing effect, or materials applied to medical purpose, perfume, coloring matter, and so on, in a kneader. As described above, bath preparations of a powder type of the present invention may be obtained.

Alternatively, the mixture, comprising the powder type cyclodextrin vitamin clathrate compound and the other raw materials of baths and stirred in the kneader, may be pressed to form blocks. The blocks may be crushed and filtered to form granular bath preparations of the present invention.

Further alternatively, the above-mentioned mixture stirred in the kneader may be subjected to compression mold by means of a tablet machine to form bath preparations of a tablet type of the present invention.

According to the present invention, the following materials may be used as the conventionally known raw materials of baths together with the cyclodextrin vitamin clathrate compound of vitamin or the cyclodextrin vitamin clathrate composition.

(A) Inorganic salts:

Sodium chloride, sodium hydrogencarbonate, sodium carbonate, borax, sodium sulfate, sodium sulfide, sodium sesquicarbonate, sodium nitrate, sodium thiosulfate, polyphosphoric acid sodium, sodium phosphate, calcium thiosulfate, calcium oxide, calcium nitrate, calcium carbonate, calcium hydrogenphosphate, potassium sulfide, potassium nitrate, potassium bromide, potassium chloride, aluminum sulfate, magnesium carbonate, heavy magnesium carbonate, ammonium chloride, iron sulfate, and so.

(B) Inorganic acids:

Boric acid, metasilicic acid, silicic acid anhydride, and so on.

(C) Organic acids:

Benzoic acid, citric acid, fumaric acid, tartaric acid, pyrrolidonecarboxylic acid, and so on.

(D) Medicinal herbs:

*Foeniculi Fructus*, extracts of *Phellodendri cortex*, Japanese Valerian, Camomile, *Scutellariae radix*, *cinnamomum cortex*, *Carthami flos, Nulpharis rhizoma*, Saffron, *Paeoniae radix*, *Houttuyniae herba*, *Zingiberis recens rhizoma*, *Acorus calamus*, *Cnidii rhizoma*, *Atractylodis lancea rhizoma*, *Aurantii nobbis percarpium*, *Angelicae radix*, Bitter Orange Peel, *Ginseng radix*, *Menthae folium*, *Angelicae dahuricae radix*, *Atractylodis rhizoma*, *Eriobotryae forium*, Hoelen, Borneol, and so on.

(E) Oils:

Olive oil, soybean oil, bran oil, extracts of rice barn oil, liquid paraffin, vaseline, and so on.

(F) Perfumes:

(i) Natural perfumes;

Lavender, jasmin, lemon, rose, orange, pine, and so on.

(ii) Synthetic perfumes;

Geraniol, citronellol, phenylethyl alcohol, benzyl acetate, and so on.

(G) Coloring matters:

Amaranth, Tartrazine, Fast Green FCF, Brilliant Blue FCF, Rhodamine B, Orange II, Uranine, Alizarine Cyanine Green F, Indigo, chlorophyll, riboflavin, annato, crocin, cochineal, safflower, anthraquinone, and so on.

(F) Alcohols:

Ethanol, stearyl alcohol, isopropyl alcohol, cetyl alcohol, hexadecyl alcohol, and so on.

(G) Polyols:

Glycerol, propylene glycol, sorbitol, and so on.

(H) Others:

Sulfur, mineral powder, incrustation of hot-spring water, neutral china clay, sodium salicylate, sodium carboxymethylcellulose, powder of yolk, roasted rice bran, powder of mica, polyvinyl pyrolidone, and so on.

The above-described raw materials of baths may be a powder type, a granule type, a tablet type, a crystal type, or a pasty type, and the medicinal herbs may remain their shapes or may be crushed.

It is preferred that the perfumes or the like are contacted with th cyclodextrin or the reduced cyclodextrin-containing syrup to form a cyclodextrin perfume clathrate compound. The cyclodextrin perfume clathrate compound is powdered, and is finally mixed with the cyclodextrin perfume clathrate compound or cyclodextrin vitamin clathrate compound of vitamins together with the other raw materials of baths. Alternatively, a small amount of cyclodextrin is mixed to the perfume to emulsify it, and the emulsion is added to liquid containing cyclodextrin vitamin clathrate compound, and it is powdered together with the cyclodextrin vitamin clathrate compound. The perfume used in the present invention is not limited, and it is preferred that flavor of milk is used in order to increase atmosphere of milk bath.

Generally speaking, the cyclodextrin clathrate compound obtained from powder cyclodextrin or cyclodextrin syrup is difficult to be dissociated, in other words, opening of rings does not occur easily, and the cyclodextrin clathrate compound under the dry conditions is not dissociated until the temperature reaches about between 80° and 130° C. Accordingly, when the bath preparations, wherein such a cyclodextrin clathrate compound is contained, are used, the bath preparations have to be dissolved in hot water prior to they are poured in bath water so as to dissociate the cyclodextrin clathrate compound. However, when hot water is used, there may be a problem that the vitamin or vitamins included in the cyclodextrin clathrate compound are easily destroyed by the heat after the cyclodextrin clathrate compound is dissociated. Therefore, it is not recommended to dissolve the cyclodextrin vitamin clathrate compound in hot water.

Accordingly, it is preferred that the rings of the cyclodextrin clathrate compound are dissociated at a temperature of usual bath and that the vitamin which was included in the cyclodextrin clathrate compound is dissolved.

The cyclodextrin clathrate compound produced from the reduced cyclodextrin syrup may be easily dissociated, i.e., opening of its rings may be easily occur. However, it is preferred that such a cyclodextrin clathrate compound is further easily dissociated.

For such a purpose, it is preferred that a very small amount of saccharifying enzyme is used with the bath preparations of the present invention. Alph-amylase, or Cyclomaltodextrin glucanotransferase, for example, may be used as the saccharifying enzyme. In this case, after the vitamin is included in the cyclodextrin and is dried to form powder, it may be mixed with the sacharifying enzyme together with other materials of the baths. Alternatively, it may be isolated from the saccharifying enzyme so that the saccharifying enzyme does not contact the cyclodextrin clathrate compound, and the saccharifying enzyme and the cyclodextrin clathrate compound may be poured together into a bath. Examples of methods for insulating the saccharifying enzyme from the cyclodextrin clathrate compound are as follows.

Example 1: The cyclodextrin clathrate compound and the saccharifying enzyme are kept in separate containers, respectively.

Example 2: The saccharifying enzyme is contained in one or more water-soluble small bags, and the bags are mixed with the cyclodextrin clathrate compound and are kept together in a container.

Example 3: Each dose of saccharifying enzyme is contained in a water-soluble small bag, and a dose of cyclodextrin clathrate compound is contained in a water-soluble container together with the water-soluble small container.

Example 4: A partition is formed in a water-soluble container to form two spaces, in one of which the cyclodextrin clathrate compound is contained and in the other of which the saccharifying enzyme is contained.

When the saccharifying enzyme thus prepared is poured into the bath, the temperature of which is about 40° C. and is suitable for the activities of the saccharifying enzyme, the saccharifying enzyme acts on the rings of the cyclodextrin clathrate compound contained in the bath preparations to open the rings. As a result, the vitamin, which has been included in the cyclodextrin vitamin clathrate compound, is dissociated and dissolved in the bath water, and the bath preparations of the present invention have effects for refreshing the skin.

EMBODIMENT 1 (Powder Type)

Forty-five parts by weight of sodium sulfate; 51 parts by weight of sodium hydrogencarbonate; 2 parts by weight of borax; 2 parts by weight of cyclodextrin vitamin clathrate compound; a small amount of perfumes; a small amount of uranine; and a small amount of saccharifying enzyme were mixed and agitated in a kneader, and a powder bath preparation was obtained.

EMBODIMENT 2 (Powder Type)

Forty-six parts by weight of sodium sesquicarbonate; 42 parts by weight of sodium chloride; 4 parts by weight of cyclodextrin vitamin clathrate compound produced from the reduced cyclodextrin syrup (perfumes were added after inclusion process); 8 parts by weight of medical herbs; and a small amount of uranine were mixed and agitated in a kneader, and a powder bath preparation was obtained. Sacharifying enzyme was stored in a container separate from the above-described mixture.

EMBODIMENT 3 (Powder Type)

Forty-four parts by weight of sodium sulfate; 50 parts by weight of sodium hydrogencarbonate; 2 parts by weight of borax; 3 parts by weight of cyclodextrin vitamin clathrate compound; 1 part by weight of carboxymethylcellulose; a small amount of perfumes; and a small amount of uranine were mixed and agitated in a kneader. The mixture was pressed to form blocks, and the blocks were crushed and sieved to form granule type bath preparations. Sacharifying enzyme was stored in water-soluble capsules, and the mixture of the capsules and the granule type bath preparations were stored in the same container.

EMBODIMENT 4 (Tablet Type)

Thirty-five parts by weight of sodium sesquicarbonate; 34 parts by weight of sodium chloride; 6 parts by weight of cyclodextrin vitamin clathrate compound (perfumes and coloring matters were added after inclusion process); 25 parts by weight of borax were mixed and agitated in a kneader, and the mixed powder was compression molded by means of a tablet machine to form tablet type bath preparations. Each dose of saccharifying enzyme was stored in a small bag.

EMBODIMENT 5 (Granule Type)

Forty-four parts by weight of sodium sulfate; 50 parts by weight of sodium hydrogencarbonate; 2 parts by weight of borax; 3 parts by weight of cyclodextrin vitamin clathrate compound produced from the reduced cyclodextrin syrup; 1 part by weight of carboxymethylcellulose; a small amount of perfumes; and a small amount of uranine were mixed and agitated in a kneader. The mixture was pressed to form blocks, and the blocks were crushed and filtered to form granule type bath preparation.

ADVANTAGES OF THE INVENTION

The bath preparations of the present invention comprise a cyclodextrin vitamin clathrate compound or a cyclodextrin clathrate of vitamins. Accordingly, the bath preparations of the present invention can achieve effects for refreshing the skin in combination with the conventional baths.

According to the present invention, vitamin or vitamins are included in the cyclodextrin. Accordingly, they are very stable and are durable against destruction or deterioration when they are mixed with or stirred with other raw materials of the baths. Accordingly, the industrial production and administration of bath preparations of the present invention is very easy.

Further, it is easy to add perfumes to the cyclodextrin vitamin clathrate compound of the present invention. The cyclodextrin clathrate compound of the present invention is readily powdered. Accordingly, it is easy to produce bath preparations from the cyclodextrin vitamin clathrate compound of or the cyclodextrin vitamin clathrate of vitamins.

Since vitamin or vitamins are included in the cyclodextrin in the bath preparations of the present invention, the vitamin or vitamins are water-soluble, and are evenly dispersed in the bath when they are poured in the water.

In addition, when the bath preparations of the present invention are used with saccharifying enzyme, the cyclodextrin clathrate compound can be readily dissociated at a temperature of usual bath, and the vitamin or vitamins included in the cyclodextrin vitamin clathrate compound are dissolved without being destroyed. Thus, the vitamin or vitamins function effectively to the skin.

When the end-groups of maltooligosaccharide syrup are almost completely reduced, and then, reduced cyclodextrin syrup, which is a mixture of the reduced syrup and cyclodextrin, is used to include vitamin or vitamins to form cyclodextrin vitamin clathrate compound or cyclodextrin vitamin clathrate compound of vitamins, the reduced cyclodextrin syrup has a more uniform dispersion capability of the cyclodextrin and the inclusion capability is increased.

When cyclodextrin containing malt syrup on the market is used to produce cyclodextrin vitamin clathrate compound of or cyclodextrin vitamin clathrate compound of vitamins, the scorching, i.e., oxidation, of syrup may occur if the treating temperature is high. As a result, there may occur a problem that the vitamin or vitamins cannot be fully included in cyclodextrin. In such a case, it is preferred that end-groups of maltooligosaccharide syrup are substantially completely reduced, and that then, the reduced cyclodextrin syrup, which is a mixture of the reduced syrup and cyclodextrin, is used to include the vitamin or vitamins to form a cyclodextrin vitamin clathrate composition or a cyclodextrin vitamin clathrate compound of the vitamins. Therefore, the syrup will not be easily oxidized, and its stability against high temperature is increased. Further, the syrup will not be easily colored, since the reaction with amino groups, such as amino acid, i.e., amino carbonyl reaction, does not occur.

When a commercially available cyclodextrin containing syrup is used to include vitamin or vitamins therein, the obtained cyclodextrin clathrate compound is not dissociated, i.e., its rings are not open, until it is heated to a relatively high temperature, for example, between 80° and 130° C. under the dry conditions. Contrary to this, when the reduced cyclodextrin syrup is used to include vitamin or vitamins therein, the produced cyclodextrin clathrate compound can be dissociated easily, and the cyclodextrin clathrate compound can be readily dispersed in water.

It is preferred that the perfumes, which are mixed with the cyclodextrin vitamin clathrate compound or the cyclodextrin vitamin clathrate compound of vitamins, are included in the reduced cyclodextrin syrup, because thus obtained cyclodextrin clathrate compound of the perfumes is preferable for bath preparations since it is stable and since it can be readily dispersed in water or warm water and dissolved therein.

What is claimed is:
1. A stable bath preparation comprising a vitamin cyclodextrin clathrate compound and a saccharifying enzyme.

2. A bath preparation according to claim 1, wherein said vitamin clathrate compound comprises at least one vitamin selected from the group consisting of vitamin A, vitamin B, vitamin C, Vitamin D, vitamin E, vitamin F and vitamin P.

3. A bath preparation according to claim 1, wherein said vitamin is in powder form.

4. A bath preparation according to claim 1, wherein said saccharifying enzyme and said cyclodextrin vitamin clathrate compound are mixed.

5. A bath preparation according to claim 1, wherein said saccharifying enzyme does not directly contact said cyclodextrin vitamin clathrate compound.

6. A bath preparation according to claim 1, wherein said bath preparation contains at least one of medicinal herb extract and at least one medicinal herb.

7. A method for producing a vitamin-containing bath preparation which comprises:
   substantially reducing end-groups of a syrup comprising maltooligosaccharide to form a reduced syrup;
   adding cyclodextrin to the reduced syrup if the cyclodextrin content is below a desired level,
   contacting at least one vitamin with the reduced syrup containing cyclodextrin, to form a cyclodextrin vitamin clathrate compound; and
   mixing said cyclodextrin vitamin clathrate compound with conventional bath materials.

8. A method for producing a bath preparation according to claim 7, wherein said at least one vitamin is selected from the group consisting of vitamin A, vitamin B, vitamin C, vitamin D, vitamin E, vitamin F and vitamin P.

9. A method for producing a bath preparation according to claim 7, wherein said syrup comprising maltooligosaccharide is hydrogenated under nickel catalyst and high pressure so as to reduce said end-groups of said maltooligosaccharide syrup.

10. A method for producing a bath preparation according to claim 7, wherein saccharifying enzyme is mixed with said cyclodextrin vitamin clathrate compound and said conventional bath materials of the bath when said mixing of said cyclodextrin vitamin clathrate compound and said conventional bath materials of the bath is carried out.

11. A method for producing a bath preparation according to claim 10, which comprises:
   contacting said vitamin with said reduced syrup comprising maltooligosaccharide and cyclodextrin to form said cyclodextrin vitamin clathrate compound;
   mixing said other conventional materials of the bath with liquid material containing said cyclodextrin vitamin clathrate compound;
   drying the mixture of said conventional materials of the bath and said cyclodextrin vitamin clathrate compound at a relatively low temperature to form a powder bath preparation containing cyclodextrin vitamin clathrate compound; and
   mixing said powder bath preparation containing cyclodextrin vitamin clathrate compound with said saccharifying enzyme, which is a powder.

12. A method for producing a bath preparation according to claim 7, which comprises:
   contacting said vitamin with said reduced syrup comprising maltooligosaccharide and cyclodextrin to form said cyclodextrin vitamin clathrate compound;
   drying said cylodextrin vitamin clathrate composition to form a powder cyclodextrin vitamin clathrate compound; and
   mixing said powder cyclodextrin vitamin clathrate compound with conventional bath materials.

13. A method for producing a bath preparation according to claim 7, which comprises:
   contacting said vitamin with said reduced syrup comprising maltooligosaccharide and cyclodextrin to form said cyclodextrin vitamin clathrate compound;
   mixing said other conventional materials of the bath with liquid material containing said cyclodextrin vitamin clathrate compound;
   drying the mixture of said conventional materials of the bath and said cyclodextrin vitamin clathrate compound at a relatively low temperature to form a powder clathrate bath preparation.

* * * * *